United States Patent [19]

Jacobs

[11] Patent Number: 5,061,282
[45] Date of Patent: Oct. 29, 1991

[54] COCHLEAR IMPLANT AUDITORY PROSTHESIS

[76] Inventor: Jared J. Jacobs, 14251 Paul Ave., Saratoga, Calif. 95070

[21] Appl. No.: 418,671

[22] Filed: Oct. 10, 1989

[51] Int. Cl.$^5$ .......................... A61F 2/18; A61N 1/00; A61B 5/04; H04R 25/00
[52] U.S. Cl. ..................... 623/10; 128/642; 128/784; 128/420.6; 600/25
[58] Field of Search .......... 600/25; 128/642, 784–789, 128/420.6; 623/10

[56] References Cited

U.S. PATENT DOCUMENTS

| | | | |
|---|---|---|---|
| 3,751,605 | 8/1973 | Michelson | 128/420.6 |
| 4,400,590 | 8/1983 | Michelson | 128/420.6 |
| 4,819,647 | 4/1989 | Byers et al. | 128/642 |
| 4,850,962 | 7/1989 | Schaefer | 128/420.6 |

OTHER PUBLICATIONS

Merzenich, Byers, White and Vivion, "Cochlear Implant Prostheses: Strategies and Progress", Annals of Biomed Engr, vol. 8, pp. 361–368; 1980.
White, Robert; "Review of Current Status of Cochlear Prostheses", pp. 233–238, IEEE Transactions on Biomedical Engr., vol. BME-29, No. 4, Apr. 1982.
Ernest Feigenbaum, M.D., "Cochlear Implant Devices for the Profoundly Hearing Impaired," IEEE Eng in Med and Biol, Jun. 1987, pp. 10–21.

Primary Examiner—Alan Cannon
Assistant Examiner—Elizabeth M. Burke
Attorney, Agent, or Firm—Flehr, Hohbach, Test, Albritton & Herbert

[57] ABSTRACT

A cochlear implant auditory prosthesis corrects sensorineural deafness by generating stimulus signals to neurons connected to the auditory nerve in response to vibrations in the basilar membrane of the cochlea of the inner ear. The prosthesis comprises a plurality of transducer elements disposed along the length of the cochlea adjacent to the basilar membrane, whereby each transducer element responds to vibrations in the basilar membrane at the corresponding location of the respective transducer element. Each transducer element comprises a transducer for detecting the respective vibrations of the basilar membrane, and a signal processing element for generating a stimulus signal in response to the vibration. The frequency response and gain of each transducer element of the prosthesis can be tuned by a compact control unit to provide an ideal response for the user.

10 Claims, 7 Drawing Sheets

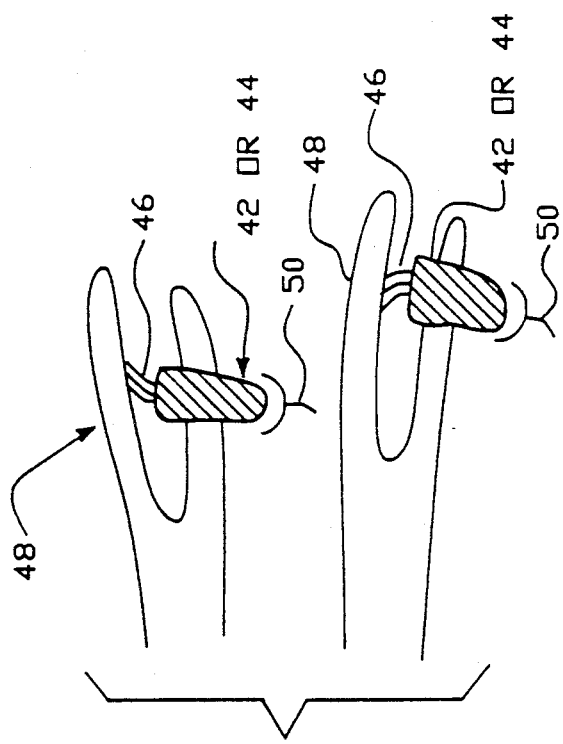
FIG.—4
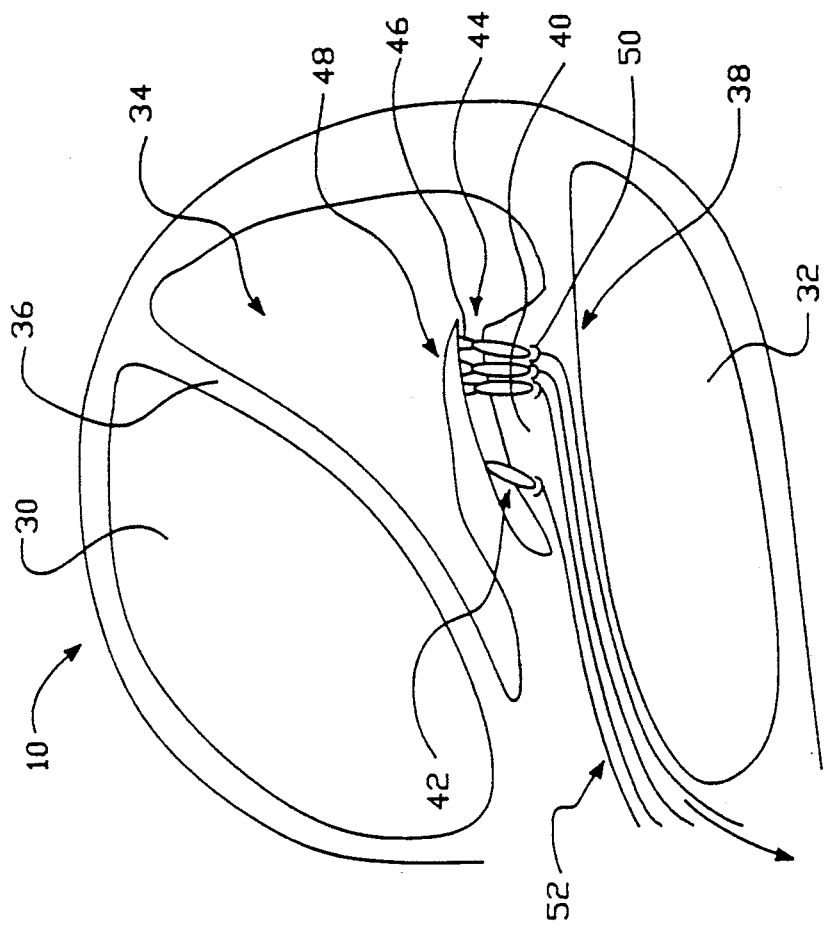
FIG.—3

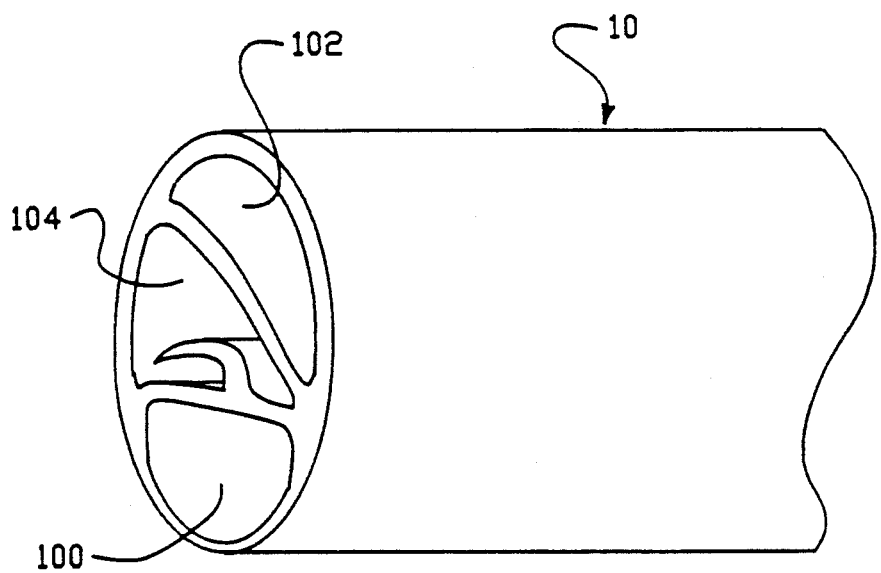
FIG.—5
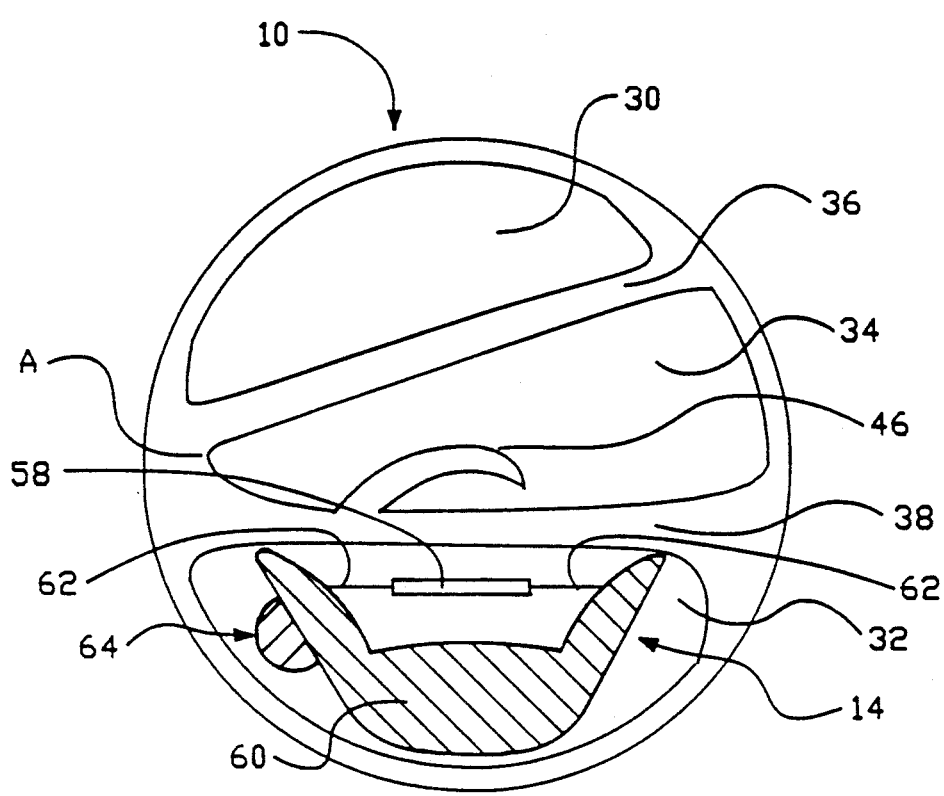
FIG.—6

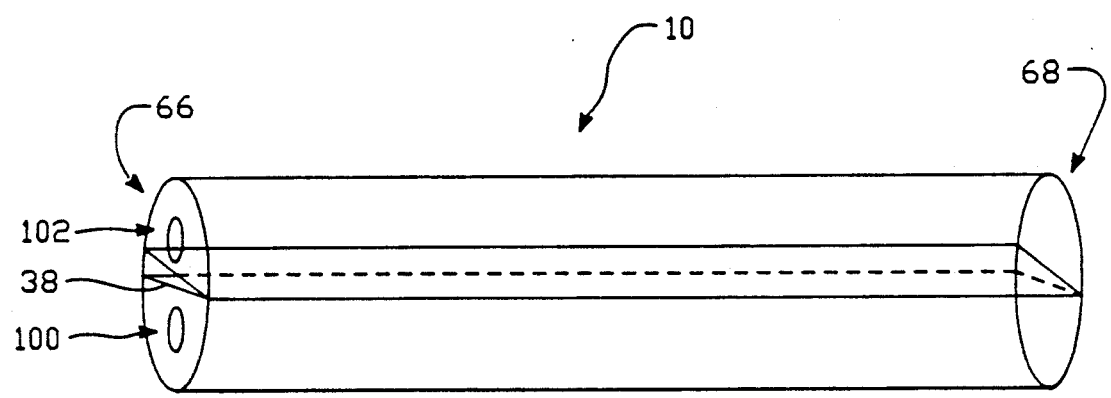
FIG.−7
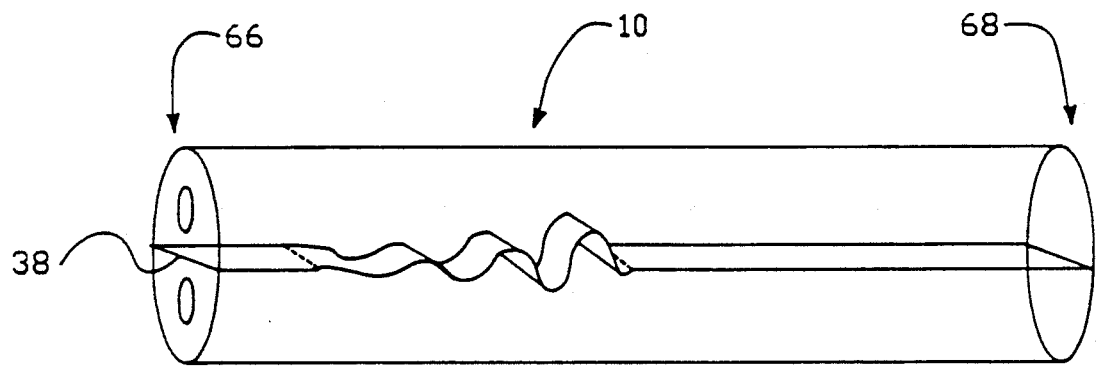
FIG.−8

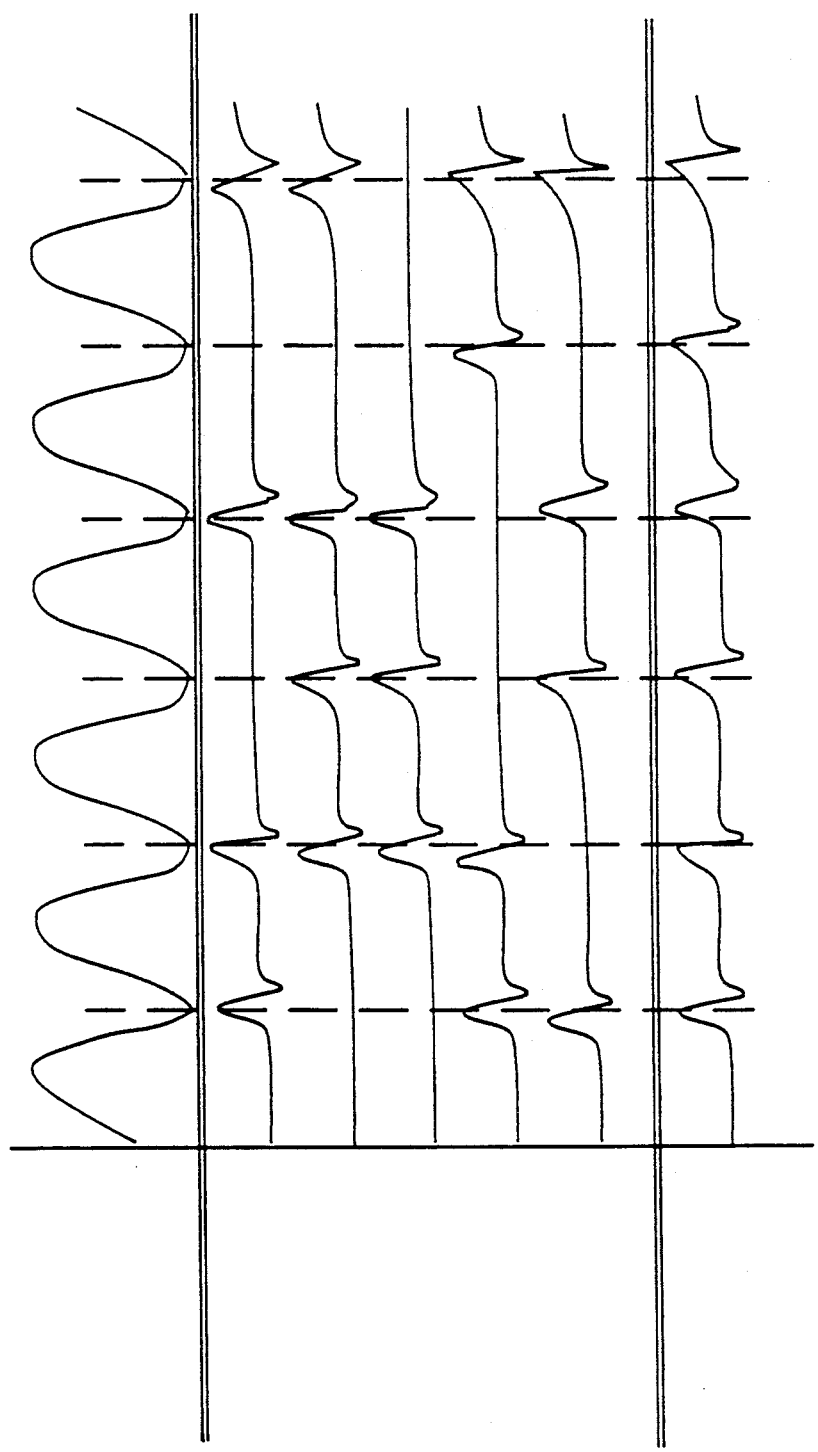
FIG.—9

COCHLEAR IMPLANT AUDITORY PROSTHESIS

BACKGROUND OF THE INVENTION

The present invention relates to a cochlear implant prosthesis for individuals who have hearing disabilities. More specifically, this invention relates to a cochlear implant auditory prosthesis for generating stimulus signals to neurons connected to the auditory nerve in persons suffering from sensorineural deafness.

DESCRIPTION OF THE RELATED ART

The cochlea is a fluid-filled organ in the inner ear which aids in the conversion of sound waves to electrochemical stimuli. In a healthy ear, sound normally travels through the external ear canal to the tympanic membrane, also known as the ear drum. The tympanic membrane vibrates in response to pressure changes in the sound waves. The vibrations are transmitted through a series of small bones in the middle ear to the cochlea, or inner ear. The innermost of the small bones, the stapes or more commonly referred to as the stirrup, contacts a membranous opening known as the oval window at the base of the cochlea. The stapes transmits sound vibrations through the oval window to the fluid-filled interior of the cochlea. These sound vibrations are then transmitted through the cochlear fluid which induces vibration in a membrane within the cochlea. This membrane, known as the basilar membrane, follows a spiral path along the length of the cochlea. Longitudinal lines of hair cells on the basilar membrane sway in response to the vibrations. The motion of the cilia of the hair cells causes alternating localized changes in electrical potential that stimulate the auditory nerve fibers. A dysfunction of these hair cells causes sensorineural deafness, whereby the hair cells respond improperly and fail to stimulate the auditory neurons.

Each auditory nerve fiber carries a specific modality of sensation to the brain. The type of sensation perceived when a sensory nerve is stimulated is determined by the specific area in the central nervous system to which the nerve fiber leads. Thus, regardless of whether the auditory nerve is stimulated by its sensory end-organ hair cell, or by direct electrical signals, a perception of sound is created. This phenomenon forms the fundamental basis of the implanted cochlear prosthesis.

Cochlear implants characteristically function by delivering electrical stimuli representative of sound to the eighth, or auditory, nerve which is responsible for transmitting impulses from the inner ear to the brain. This is accomplished by the transformation of sound and speech information into electrical signals that create auditory perceptions upon their application to the auditory nerve.

Cochlear implants are intended for patients with sensorineural deafness, since conventional hearing aids are no longer useful. Conventional cochlear implants attempt to correct deafness by using an electrical device capable of generating a stimulus in the neurons normally acted upon by the hair cells. As disclosed in FIG. 12, a conventional implant 54 is inserted into the cochlea 10 via the round window 100 and includes electrodes 56 which may be, for example, equidistantly spaced at intervals along the length of the cochlea 10. These electrodes 56 receive signals from additional electronic devices stored in another part of the implant 54, as well as from an external acoustic transmitter/receiver worn on the body of the user of the implant. The external acoustic transmitter/receiver picks up sound waves from the environment and modifies them for speech recognition purposes. The resulting speech data is then transmitted to electronics implanted in the skull of the user. The implanted electronic circuitry then sends signals to the appropriate electrodes 56 to indirectly stimulate the associated neurons, with the objective that they are interpreted as sound by the brain.

In the past, the results of the cochlear implants have not always proven effective. Users of the implants usually cannot interpret speech without relying on lip reading, thus making telephone use impossible. Further, users who previously had hearing ability often perceive the sound induced by the implant to be different from the sound they had perceived prior to deafness. Thus, the users suffer the additional burden of learning to correlate the new sounds to their environment. Finally, users must suffer the inconvenience of wearing an external acoustic transmitter/receiver as well as associated electronics.

These difficulties are not intended to be exhaustive but rather are among many which tend to reduce the effectiveness and user satisfaction with prior cochlear implants.

SUMMARY OF THE INVENTION

It is therefore an object of the present invention to provide a novel cochlear implant apparatus which is simple in structure, thus facilitating the implantation process, as well as making the apparatus more convenient for the user.

It is another object of the present invention to provide a cochlear implant apparatus which provides a more accurate representation of the perceived sound over the entire audible frequency range.

It is an additional object of the present invention to provide a cochlear implant apparatus which allows spatial and temporal adjustments with respect to specific frequencies.

It is still an additional object of the present invention to provide a cochlear implant apparatus which more accurately simulates the damaged hair cells, thereby eliminating the necessity for an external speech processor or acoustic transmitter/receiver.

Finally, it is an object of the present invention to provide a cochlear implant apparatus that does not require electronics to be implanted in the skull of a user, thereby reducing the complexity of the implantation process, as well as improving the reliability and cost-effectiveness of the implant.

In order to achieve these and other objects, the present invention provides a cochlear implant auditory prosthesis which simulates the functions of hair cells. The cochlear implant auditory prosthesis comprises a plurality of transducer elements operable to be disposed along the length of the cochlea adjacent to the basilar membrane. Each transducer element is responsive to vibrations in the basilar membrane at the corresponding location of the respective transducer element. Upon detection of the vibration at the particular location on the basilar membrane, the transducer element performs a predetermined modulation and, if desirable, generates a signal to stimulate the corresponding nerve via an electrode. The modulation is determined by the location of the transducer element along the basilar membrane, as well as the desired frequency response and individual user requirements. Thus, by controlling the transducer element, the cochlear implant auditory prosthesis of the present invention may be tuned to provide an ideal response for the user.

The simplified structure of the cochlear implant auditory prosthesis of the present invention provides numerous advantages over conventional implants. The cochlear prosthesis of the present invention does not require an external acoustic receiver/transmitter to send speech signals to the implant. Further, it does not require a speech analysis unit since it allows the completely functional Basilar Membrane, and the transducer element's direct response to the movement of the membrane, to determine the charge at the electrodes.

Finally, no electrical components other than a battery need to be implanted in the skull of the patient. Thus, complexity of the implantation process is greatly reduced, and the reliability and cost-effectiveness of the implant is greatly improved.

BRIEF DESCRIPTION OF THE DRAWINGS

Other objects and advantages of the present invention will become apparent from the following detailed description of a preferred embodiment thereof in conjunction with the accompanying drawings, wherein:

FIG. 3 is a cross-sectional detail view of a normal cochlea of the inner ear, as well as the basilar membrane, hair cells and nerve fibers associated therewith;

FIG. 4 is a schematic view disclosing the displacement of the cilia of a normal hair cell;

FIG. 5 is a schematic perspective view disclosing the terminus of the cochlea;

FIG. 6 is a cross-sectional view of the cochlea including a transducer element of the present cochlear implant auditory prosthesis positioned therein in accordance with a preferred embodiment of the invention;

FIG. 7 is a schematic view of the cochlea extended longitudinally to disclose the frequency response ranges of the basilar membrane;

FIG. 8 is a schematic view of the cochlea extended longitudinally to disclose the absorption of sound wave energy by the basilar membrane of an inner ear.

FIG. 9 is a graphical representation of the response in the eighth cranial nerve to an acoustic stimulus.

DETAILED DESCRIPTION OF THE PREFERRED EMBODIMENT

Figure 1:
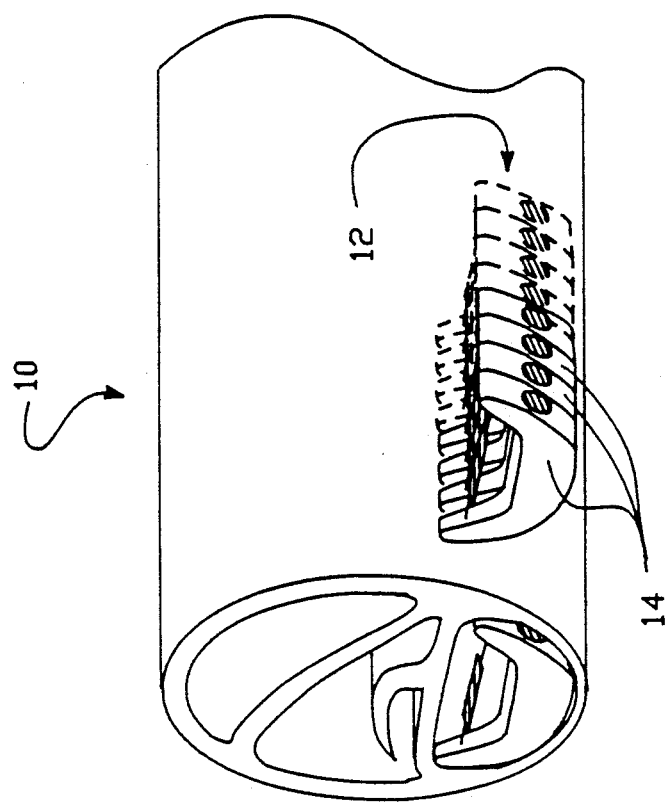
FIG. 1 is a perspective view of the cochlea of a patient's inner ear with the cochlear implant auditory prosthesis positioned therein according to a preferred embodiment of the invention.

Referring to FIG. 1, the cochlea 10 of patient's inner ear is shown having a cochlear auditory prosthesis 12 implanted therein, in accordance with a preferred embodiment of the invention. The cochlear auditory prosthesis 12 comprises a plurality of transducer elements 14 which translate mechanical vibrations to electrical signals to stimulate the respective neurons in order to provide a hearing sensation to patients suffering from sensorineural deafness. Here, it is shown that each transducer element 14 is electronically independent from adjacent transducer elements, and, therefore, can generate localized electrical impulses along the entire length of the cochlea 10 as a result of localized input from the basilar membrane.

Figure 2:
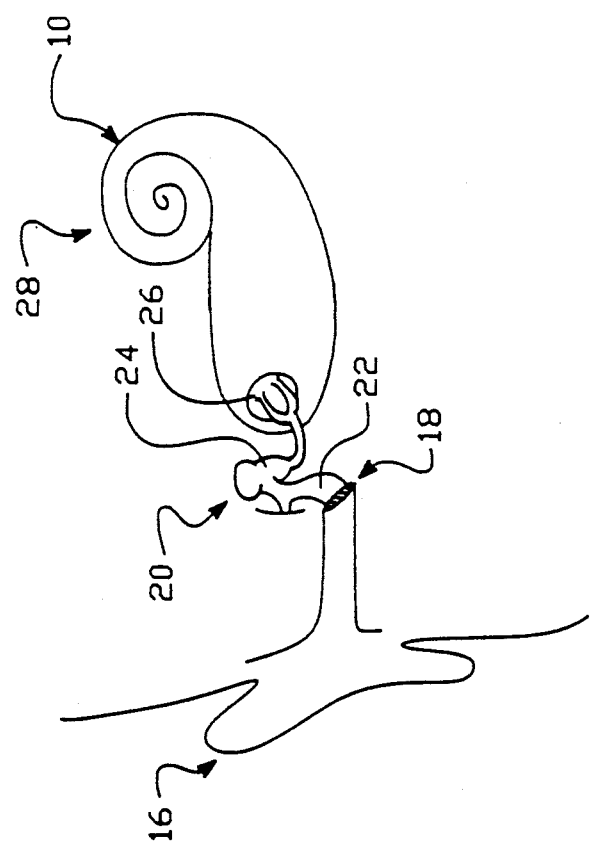
FIG. 2 is a schematic view of the outer, middle and inner ear including the cochlea, the tympanic membrane and the stapes.

In order to fully appreciate the advantages of the cochlear implant auditory prosthesis, FIGS. 2-4 have been included herein to provide background on the anatomy of the ear in conjunction with the mechanism of auditory reception.

FIG. 2 discloses the basic structure of the outer, middle and inner ear. As sound waves enter the outer ear 16, the waves modify the shape of the tympanic membrane 18, commonly known as the ear drum. This change in shape of the tympanic membrane 18 corresponds to pressure changes in the sound wave. The pressure on the tympanic membrane 18 is applied directly to three ossicles located in the middle ear 20. The three ossicles, namely the malleus 22 (the mallet), the incus 24 (the anvil) and the stapes 26 (the stirrup) vibrate in response to the pressure changes and ultimately apply pressure to the cochlea 10 via the last of these ossicles, the stapes 26. The cochlea 10 itself is a coil-shaped structure located in the inner ear 28 and is the primary location for the transformation of sound waves to electrical stimuli.

As seen in FIG. 3, the cochlea 10 has three parallel canals which spiral along its length: the scala vestibuli 30, the scala tympani 32 and the scala media 34. The scala vestibuli 30 and scala media 34 are separated longitudinally throughout the cochlea 10 by an extremely thin partition known as the vestibular membrane 36. The scala vestibuli 30 and the scala tympani 32 are continuous at their distal ends and filled with "perilymph", fluid found within the cochlea 10. The scala vestibuli 30 and scala tympani 32 are separated by the basilar membrane 38 which supports a structure known as the "Organ of Corti" 40 along its length. Mechanically sensitive inner 42 and outer 44 hair cells are part of the organ of Corti 40. The hair cells 42 and 44 have cilia 46 at one end which flagellate and lightly contact a tectorial membrane 48. At an opposed end, the hair cells 42 and 44 are slightly distanced from the distal end 50 of nerve fibers 52. These nerve fibers 52 conjoin with the eighth cranial nerve which, in turn, leads to the brain.

As shown in FIG. 5, the cochlea 10 has three small openings at its base: the fenestra cochleae (round window) 100, the fenestra vestibuli (oval window) 102 and a smaller inferior canal opening 104. The round window 100 provides entry into the scala tympani 32, while the oval window 102 opens into the scala vestibuli 30. Contact between the stapes 26 of the middle ear 20 and the cochlea 10 of the inner ear 28 occurs at the oval window 102.

As sound waves modify the shape of the tympanic membrane 18, the stapes 26 applies pressure to the oval window 102, and transmits this pressure to the fluid-filled scala vestibuli 30, which lies on the opposite side of the oval window; this applied pressure corresponds to changes in the sound wave. The sound-generated pressure waves which move through the perilymph in the scala vestibuli 30 cause the basilar membrane 38 to move. As a result, the basilar membrane 38 selectively vibrates with the greatest amplitude at a particular point which is mechanically tuned to the frequency of the applied sound. A complex sound will cause the basilar membrane 38 to vibrate at multiple points along its length.

This displacement of the basilar membrane 38 applies pressure to the perilymph in the scala tympani 32 on the round window side of the basilar membrane 38. This pressure forces the membranous round window 100 to flex relative to the intensity of the sound pressure. Thus, the oval window 102 and the round window 100 respond inversely to the pressure applied by the stapes 26.

As noted previously, the basilar membrane 38 is the location of mechanical-electrical transduction. Hair cells 42 and 44 on the basilar membrane 38 function as sensory end organs to generate auditory nerve impulses. In this connection, the displacement of the hair cells 42 and 44 transform the pressure-induced mechanical motion into electrical stimuli.

As disclosed in FIG. 4, the cilia 46 of the hair cells 42 and 44 brush against the tectorial membrane 48. The motion of the tectorial membrane 48 is assumed to be slightly different from the motion of the hair cells 42 and 44. As a result, the differential causes the cilia 46 of the hair cells 42 and 44 to be displaced, thus causing a depolarization of the corresponding area of the hair cell 42 or 44. When the hair cell 42 or 44 depolarizes, the distal end 50 of the corresponding nerve fiber is stimulated, which may lead to a perceived stimulus in the listener.

In sensorineural deafness, a patient suffers damage to the hair cells 42 and 44 in the cochlea 10. In this event, the cilia 46 of the hair cells 42 and 44 can no longer stimulate the corresponding neurons 50, and consequently the patient may suffer a hearing loss.

FIG. 6 shows a cross-section of a preferred embodiment of the cochlear auditory prosthesis 12 including a transducer element 14 implanted within the cochlea 10. A strip of piezoelectric film 58 is loosely stretched between the tips of a v-shaped support structure 60 of the transducer element 14. Conducting leads 62 are attached to both ends of the film 58 and are directed into electronics located within the bottom of the v-shaped support structure 60. An exposed electrode 64 is connected to the electronics and lies on one side of the v-shaped support 60. Accordingly, the side of the v-shaped support structure 60 on which the electrode 64 is mounted is placed adjacent to the tissue closest to the eighth cranial nerve. Further, the entire auditory prosthesis 12, with the exception of the electrode 64, is covered in a protective coating, such as Silastic.

The strip of piezoelectric film 58 is preferred in consideration of design aesthetics; however, other types of transducers may be utilized in the present cochlear implant auditory prosthesis 12.

The support structure 60 of the transducer element 14 is v-shaped so that each transducer element 14 will remain stable without excessive damping of the movement of the basilar membrane 38. The basilar membrane 38 is minimally damped because the only points of contact between the transducer element 14 and the basilar membrane 38 are at the union of the basilar membrane 38 and the bony cochlear shell at locations designated A. Further, only selected transducer elements 14 need contact the basilar membrane 38; thus, most transducer elements 14 are constructed so that the distance from top to bottom is less than maximum, and are held in place by adjacent transducer elements 14. While the transducer elements 14 are physically linked, each transducer element 14 has its own electronic circuitry.

The action of the input sound wave in the perilymph of the scala vestibuli 30 causes the basilar membrane 38 to move in an oscillating manner responsive to the input sound wave. This input wave is communicated through the basilar membrane 38 to the perilymph in the scala tympani 32. As the perilymph moves, its pressure impinges upon the loosely strung strips of piezoelectric film 58, thereby displacing the film 58. This displacement causes a charge to be delivered to the electronics housed in the v-shaped support structure 60 via the conducting leads 62. The transducer electronics in turn create a proportional charge and deliver the charge to the electrode 64. The electrode 64 then stimulates the corresponding nerve fiber. Since the vibration of the basilar membrane 38 in response to a given frequency varies along its length, the strength of the charge delivered to the nerve fibers is both spatially and temporally dependent.

As disclosed in FIG. 7, the portion 66 of the basilar membrane 38 near the oval window 102 resonates with high frequencies, and the portion 68 near the apical end of the basilar membrane 38 resonates with low frequencies. In relation to the transduction of sound, a sound wave moves from the high frequency (basal) end 66 of the cochlea 10 to the low frequency end (apical) 68. The basilar membrane 38 will vibrate slightly at the basal end 66 at the origin of vibration, and the amplitude of the wave on the basilar membrane 38 will increase until a point on the basilar membrane 38 is reached having optimum resonance with the frequency of the sound. At this point, most of the energy of the wave dissipates into the resonating membrane 38.

FIG. 8 shows the absorption of sound wave energy in the basilar membrane 38. Section 1 vibrates only slightly, and, therefore, the piezoelectric film 58 responding to the motion of the basilar membrane 38 will move only slightly. Section 2 delineates the area of the basilar membrane 38 which resonates with the incoming sound wave. Here, the amplitude of the vibration of the piezoelectric film 58 will be greatest. Section 3 shows little or no response to the minimal remaining energy of the sound wave, and, therefore, the piezoelectric film 58 will undergo little or no vibration.

In the 200 to 2000 Hz range, hair cells normally respond in a phase-locked fashion to the incoming sound wave. Though the firing of hair cells is phase-locked in this range, hair cells do not respond to each cycle of sound. Thus, a plurality of nerve fibers are used to respond to different cycles of the sound wave.

FIG. 9 shows the response in the eighth cranial nerve to an input acoustic stimulus; more specifically, FIG. 9 shows the waveform of an input tone, the firing rates and timing of five nerve fibers and the total accumulated response from the nerve cells in the eighth cranial nerve.

If the basilar membrane 38 vibrates in time with the input tone, and the vibrations cause the insulated strip of piezoelectric film 58 to move in time with the vibrations, then the piezoelectric film 58 will generate a current with each half cycle of the tone. One current is generated as the vibration forces the film 58 down, and another current is generated as the vibration pulls up on the film 58. In this connection, the electronics associated with each transducer element 14 must be capable of responding to only one of the two half cycles of the input frequency. Further, each transducer element 14 must ensure that the electronics trigger only at a specific point in the chosen half cycle. The direction of the motion of the film 58 may be used to determine the half cycle since the polarity of the charge output by the film 58 is dependent upon the direction of the displacement of the film 58.

If, in addition to the above, the charge emitted by the electrode 64 can be properly tuned, then the need for speech analysis may be eliminated entirely. On the other hand, if the patient seems to be responding well to specific frequencies and poorly to others, then it is possible to adjust this response by using an external hearing aid in conjunction with the cochlear auditory implant prosthesis of the present invention. By using a series of high frequency, low frequency or bandpass filters, the hearing aid can increase or decrease the amplitudes of specific incoming frequency ranges. The increased amplitude is used when the patient complains of poor response, whereas the decreased amplitude is used when the patient claims the response is too intense.

Figures 10, 11:
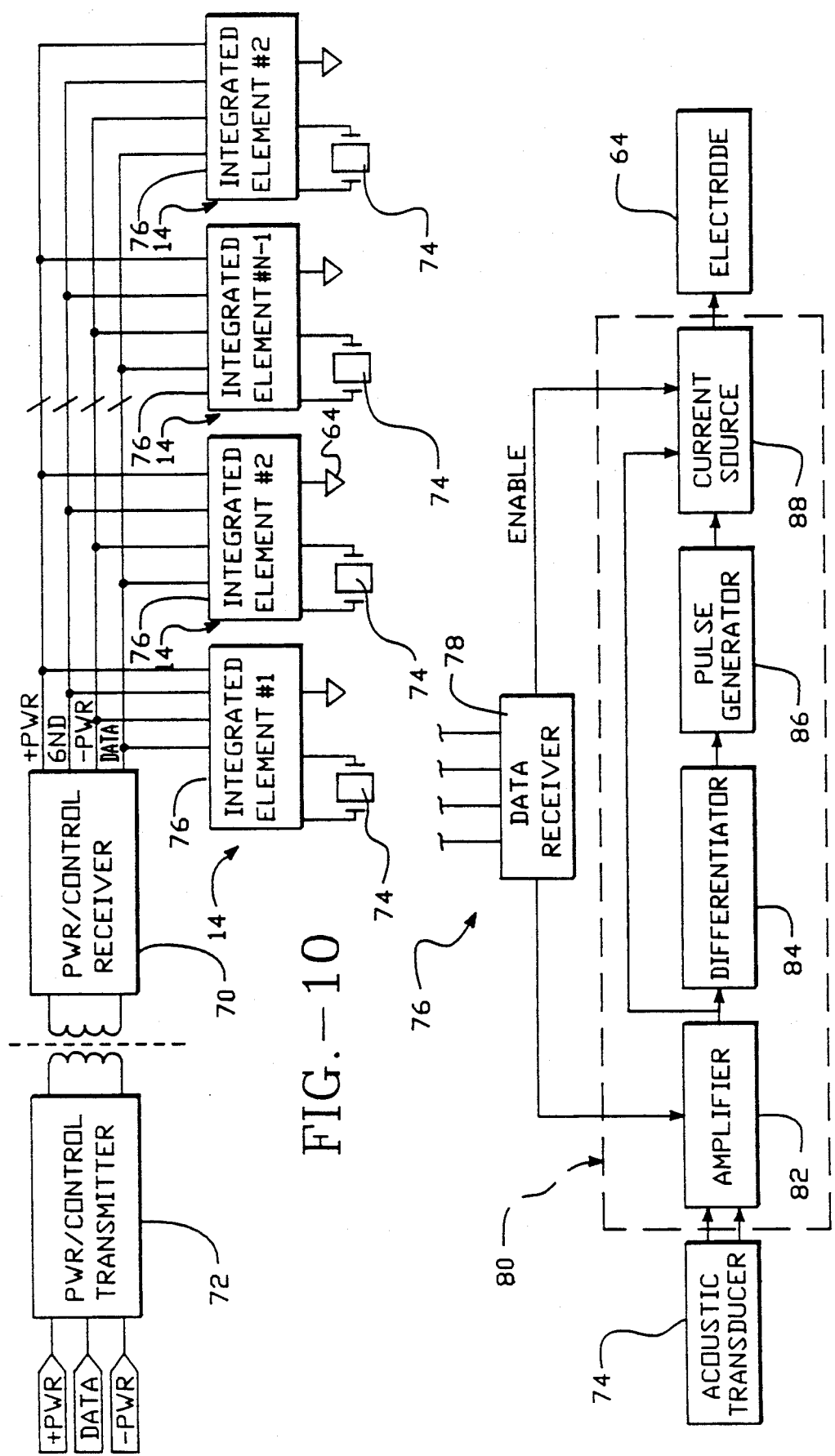
FIG. 10 is a block diagram of the preferred embodiment of the present invention showing, in part, a plurality of transducer elements.
FIG. 11 is a block diagram of an integrated element of the preferred embodiment.
Figure 12:
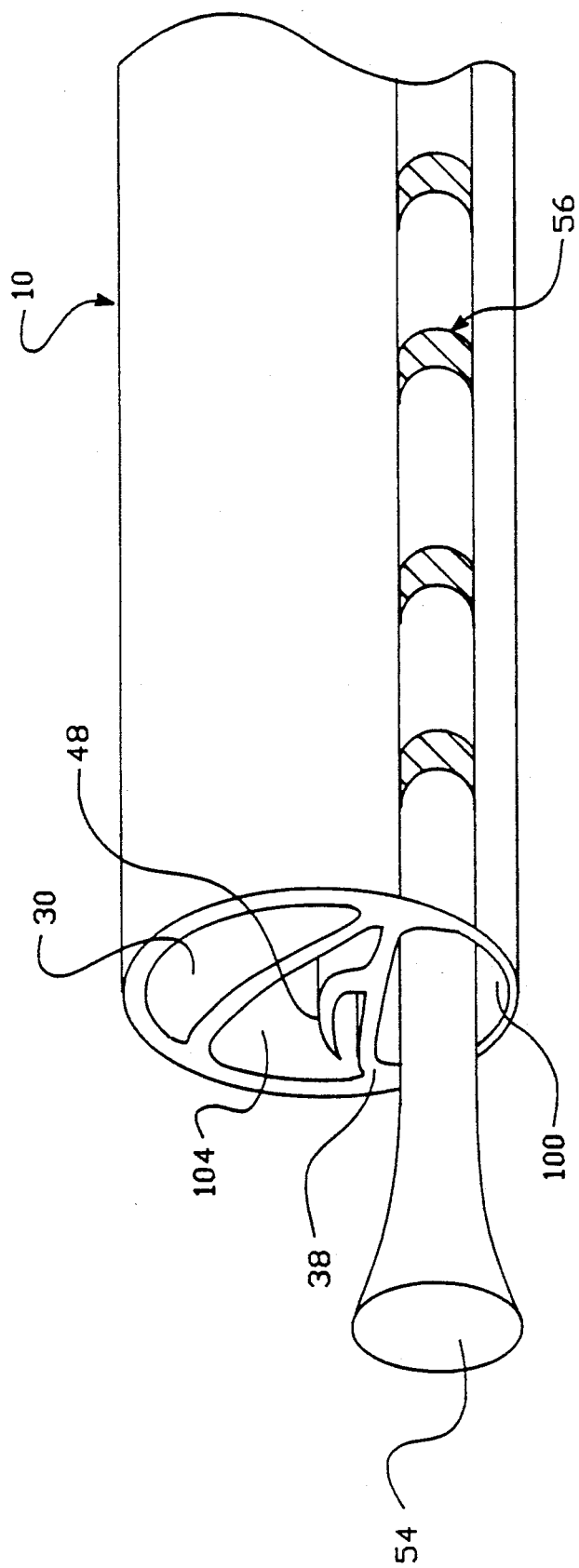
FIG. 12 is a schematic perspective view disclosing a conventional cochlear implant apparatus positioned within the cochlea.

FIGS. 10 and 11 disclose the electronics associated with the cochlear auditory prosthesis 12. Specifically, FIG. 10 discloses a plurality of transducer elements 14 each being connected to a power/control receiver 70, which receives power and data control signals from a power/control transmitter 72. The power/control transmitter 72 may include, for example, a single IC chip and a low power source, and may be designed in a compact manner to minimize inconvenience to the user. Each transducer element 14 comprises a transducer 74, for example a piezoelectric film 58, for detecting vibrations of the basilar membrane 38 at the corresponding location of each transducer element 14. The transducer 74 outputs a first signal in response to the detected vibrations of the basilar membrane 38. Each transducer element 14 further includes an integrated element 76 which generates a stimulus signal in response to the first signal. The stimulus signal is output via an electrode 64 to a corresponding neuron.

Each integrated element 76 is adjusted by a power/control transmitter 72 which sends a control signal to the power/control receiver 70. In response to the control signal, the power/control receiver 70 outputs a data signal having control and timing information to each integrated element 76. This data signal adjusts the frequency response of the cochlear implant auditory prosthesis by adjusting the charge emitted by each integrated element 76 to the respective electrode 64 in accordance with the location of the corresponding transducer element 14.

As shown in FIGURE 11, each integrated element 76 of the respective transducer element 14 comprises a data receiver 78 and a signal processing circuit 80. The data receiver 78 controls the respective transducer element 14 by outputting a second signal, such as a gain control signal, in response to the information received by the power/control receiver 70; the data receiver 78 may also output an output enable signal to further control the signal processing circuit 80. Thus, the signal processing circuit 80 generates the stimulus signal preferably in response to the first signal and the second signal, and possibly also in response to the output enable signal. The electrode 64 transmits the stimulus signal to the corresponding neuron.

The signal processing circuit 80 includes an amplifier 82, a differentiator 84, a pulse generator 86 and an output amplifier 88. The amplifier 82 generates an amplified first signal in response to the first signal from the transducer 74 and the second signal from the data receiver 78. The frequency response of the amplifier may be modified in response to the second signal; thus, the amplifier 82 may have, for example, a narrow band filter which limits amplification of the first signal to the narrow band vibrations at the desired frequency range corresponding to the location of the transducer element 14. The differentiator 84 receives the amplified first signal and in turn generates a differential signal. The pulse generator 86 outputs a third signal in response to the differential signal, to be communicated to the output amplifier 88. The differential signal triggers pulses in the pulse generator 86 at its peak amplitude. The pulse frequency of the third signal output by the pulse generator 86 is limited by the pulse duration. Finally, the output amplifier 88 generates the stimulus signal in response to the amplified first signal, the output enable signal and the third signal. The stimulus signal generated by the output amplifier 88 stimulates the corresponding neuron via the electrode 64. In this manner, the mechanical transduction of sound waves is converted to an electrical signal representative of the depolarization of hair cells.

The cochlear implant auditory prosthesis of the present invention provides several distinct advantages over prior cochlear implants: the unique combination of a plurality of flexible, electronically independent transducer elements 14 eliminate the necessity for an external acoustic receiver/transmitter for transmitting speech signals, thus adding simplicity to the structure of the implant, and making the apparatus more comfortable to the patient. Moreover, no electronics need be implanted into the skull of a patient, further reducing the complexity of the implantation process, as well as improving the reliability and cost-effectiveness of the cochlear implant auditory prosthesis 12.

The transducer elements 14 are positioned adjacent to one another along the entire length of the basilar membrane 38, thus providing a more accurate representation of the perceived sound over the entire audible range. Additionally, a power/control transmitter 72 may be incorporated into the cochlear implant auditory apparatus 12 to receive an externally input control signal indicating tuning requirements for specific transducer elements 14. The data from this control signal is transferred to a power/control receiver 70 which in turn transfers the data to the appropriate transducer element 14. In this manner, spatial and temporal adjustments may be controlled with respect to specific frequencies. In addition, the firing time of the transducer elements 14 may also be regulated.

Further, the proximity of the electrodes 64 to one another serves to more accurately simulate the damaged hair cells, thereby eliminating the need for an external speech processor.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What I claim is:

1. A cochlear implant auditory prosthesis comprising a plurality of transducer elements, each transducer element comprising:

detection means for detecting vibrations of a basilar membrane of a cochlea at a corresponding location, said detection means outputting a first signal in response to said vibrations; and signal generating means for outputting a stimulus signal to a corresponding neuron connected to an eighth cranial nerve in response to said first signal;

wherein said plurality of transducer elements are disposed along said basilar membrane at said corresponding locations.

2. A cochlear implant auditory prosthesis as recited in claim 1, further comprising control means for adjusting each transducer element in accordance with the corresponding location of the transducer element, the control means outputting a data signal.

3. A cochlear implant auditory prosthesis as recited in claim 2, wherein said signal generating means comprises:

signal control means, responsive to said data signal, for controlling said transducer element in accordance with said control means, said signal control means outputting a second signal;

signal processing means for generating said stimulus signal in response to said first and second signals; and an electrode disposed adjacent to said corresponding neuron, said electrode providing said stimulus to said neuron.

4. A cochlear implant auditory prosthesis as recited in claim 3, wherein said signal processing means comprises:

an amplifier, responsive to the second signal of said signal control means, for generating an amplified first signal in response to said first signal;

pulse generation means for generating a third signal, said pulse generating means generating said third signal in accordance with said amplified first signal, said pulse generating means comprising:

a differentiator for generating a differential signal in response to said amplified first signal, a pulse generator for generating said third signal having a pulse frequency in accordance with said differential signal, and an output amplifier for generating said stimulus signal in response to said amplified first signal, said third signal and said signal control means.

5. A cochlear implant auditory prosthesis as recited in claim 4, wherein the second signal varies a frequency response of the amplifier.

6. A cochlear implant auditory prosthesis as recited in claim 2, wherein said control means comprises:

power/control transmitter means for transmitting control and timing information to said signal generating means, said power/control transmitter means outputting a control signal and being disposed on an external side of a user; and power/control receiver means for generating said data signal in response to said control signal, said power/control receiver means being disposed on an internal side of said user.

7. A cochlear implant auditory prosthesis as recited in claim 1, wherein each transducer element further comprises:

a v-shaped support structure having a first and second end, said signal generating means being disposed within said v-shaped support structure; and an electrode for providing said corresponding stimulus signal to said neuron.

8. A cochlear implant auditory prosthesis as recited in claim 7, wherein said detection means comprises:

a strip of piezoelectric film for generating said first signal; and conducting means for transmitting said first signal to said first and second end of said v-shaped support structure.

9. A cochlear implant auditory prosthesis as recited in claim 8, wherein the first and second ends of the v-shaped support structure of at least one of said transducer support structure of at least one of said transducer elements contacts said basilar membrane at a contact location, said contact location being defined as a union of the basilar membrane and a bony cochlear shell.

10. A cochlear implant auditory prosthesis as recited in claim 1, wherein each transducer element is enclosed in a protective coating.

* * * * *